United States Patent [19]

Pomper et al.

[11] Patent Number: 4,797,365

[45] Date of Patent: Jan. 10, 1989

[54] ACTIVE DRIED YEAST

[75] Inventors: Seymour Pomper, Stamford; Gary W. Cole, Ridgefield, both of Conn.; James R. Davis, Yorktown Heights, N.Y.

[73] Assignee: Nabisco Brands, Inc., Parsippany, N.J.

[21] Appl. No.: 693,045

[22] Filed: Jan. 22, 1985

[51] Int. Cl.$^4$ .............................................. C12N 1/18
[52] U.S. Cl. ...................................... 435/256; 426/62
[58] Field of Search ........................... 426/62; 435/256

[56] References Cited

U.S. PATENT DOCUMENTS

| | | | |
|---|---|---|---|
| 2,947,668 | 8/1960 | Kuestler et al. | 426/62 |
| 3,843,800 | 10/1974 | Langejan | 426/62 X |
| 3,993,783 | 11/1976 | Langejan et al. | 426/62 X |
| 4,160,040 | 7/1979 | Luca et al. | 426/62 |
| 4,217,420 | 8/1980 | Langejan | 426/62 X |
| 4,341,871 | 7/1982 | Langejan | 426/62 X |
| 4,370,420 | 1/1983 | Clement et al. | 426/62 X |
| 4,405,650 | 9/1983 | Spadafora | 426/62 |

*Primary Examiner*—Joseph Golian
*Attorney, Agent, or Firm*—Richard Kornutik

[57] ABSTRACT

Active dried yeast is prepared using an osmotically active aqueous solution of a water soluble salt of magnesium or calcium in an initial salt treatment of the yeast cream. The resulting active dried yeast shows greater retention of activity in the final drying step than corresponding active dried yeasts obtained using osmotically active solutions of sodium and potassium salts in the same first step.

10 Claims, No Drawings

ACTIVE DRIED YEAST

BACKGROUND OF THE INVENTION

This invention relates to the preparation of active dried yeasts, and is more particularly concerned with active dried yeasts, having improved leavening activity and with processes for their preparation.

Active dried yeasts are prepared by fermentation of the appropriate strain of yeast in the presence of necessary nutrients, followed by isolation of the yeast cells from the fermentation broth to obtain a yeast cream, dewatering the yeast cream by filtration, and drying of the resulting yeast filter cake under controlled conditions.

Dewatering the yeast cream prior to drying is typically carried out by either a filter press or vacuum filtration. When using a vacuum filter to dewater the yeast cream, an important step involves treating the yeast cream with an aqueous solution of a salt such as sodium chloride, potassium chloride, or the like, which by osmotic action, forces water from the cells of the yeast. After such treatment, the majority of the external aqueous solution is separated from the wet yeast by filtration, during which process the yeast is washed with water to remove excess salt.

The compressed yeast is then subjected to drying by any of a variety of techniques such as those described in U.S. Pat. No. 3,617,306 which exemplifies the so-called "spaghetti" method. Alternative procedures for drying of yeast are described, for example, in U.S. Pat. Nos. 3,843,800 and 4,217,420.

A wide variety of osmotic solutions have been employed previously in order to force water from the cells of yeast by osmotic action. Illustratively, U.S. Pat. No. 2,947,668 teaches the use of water soluble salts of sodium, potassium, ammonium, calcium, magnesium and aluminum as well as non-electrolytes such as water soluble mono and polyhydric alcohols. The use of these various osmotic agents was contemplated by the above-identified reference in the preparation of compressed yeast rather than active dried yeast. The two forms of yeast are prepared from different types of cultures. The type of culture generally utilized in the preparation of compressed yeast products is classified as Bios No. 236 while that generally utilized in the preparation of active dried yeast is classified as Bios No. 23. These classifications are made according to the bios response procedure published by Schultz and Atkin in "Archives of Biochemistry" Vol. 14, p. 369, Aug., 1947.

The osmotic agent is selected typically on the basis of cost and osmotic potential. Those most commonly employed in the art are potassium and sodium chlorides. It is well recognized in the art that the production of active dried yeast by drying of yeast cake in the above-identified manner is accompanied by significant loss of activity (as determined by standard tests). However, it has not been previously recognized that the choice of the particular salts employed in the initial treatment of the yeast cream can play a part in controlling the loss of activity in the drying process to produce active dried yeast.

We have now found that the use of certain divalent metal salts in the solutions used to remove water from the yeast cells by osmotic action can substantially reduce, and in many cases, eliminate the loss in activity encountered hitherto in the drying process required to produce active dried yeast.

SUMMARY OF THE INVENTION

This invention comprises an improved process for preparing an active dried yeast which process comprises the steps of treating a yeast cream with a salt solution, filtering to separate yeast from the yeast cream, washing the separated yeast with water, and drying the washed yeast, wherein the improvement comprises employing as the said salt solution an aqueous solution comprising a salt of calcium or magnesium.

The invention also comprises the active dried yeast of improved activity, especially as prepared in accordance with the above process.

DETAILED DESCRIPTION OF THE INVENTION

The process of the invention is carried out utilizing the procedures hitherto employed in the art in the preparation of active dried yeast, the novel feature of the process lying in the nature of the osmotically active agent employed in the initial treatment of the yeast cream to reduce the intracellular water content of the yeast. Thus, in accordance with the process of the invention, it has been found that the use of a soluble salt of calcium or magnesium in this step enables one to produce an active dried yeast without suffering any significant loss of activity in the drying step.

Any of the edible water-soluble salts of calcium or magnesium can be employed. Illustrative of such salts are calcium chloride, magnesium chloride, calcium sulfate, calcium nitrate, monocalcium phosphate, magnesium sulfate, magnesium nitrate, magnesium ammonium chloride, and the like. The preferred salts are calcium chloride and magnesium chloride. The calcium or magnesium salts (mixtures of both magnesium and calcium salts can be used if desired) are employed in amounts such that the proportion of cation ($Ca^{++}$; $Mg^{++}$) by weight based on yeast cream is within the range of about 0.1 percent to about 5 percent and preferably within the range of about 0.2 percent to about 2 percent. The most preferred concentration of calcium or magnesium ions is from about 0.5 percent to about 1.0 percent by weight based on weight of yeast cream employed. The salts are preferably added to the yeast cream in the form of an aqueous solution.

Any of these calcium or magnesium salts can be employed alone or in combination with another member of the group. Moreover, it is possible to employ them in combination with other osmotic agents such as sodium chloride or potassium chloride so long as the calcium and/or magnesium salt or salts are present in amounts effective to achieve the improved results offered by the present invention.

As stated previously, apart from the nature of the salt used in initial treatment of the yeast cream in the manner described above, the process of the invention is carried out in accordance with the procedures commonly used in the art of preparing active dried yeast.

Thus the yeast is propagated in accordance with standard procedures such as those described, for example, in U.S. Pat. No. 3,617,306. The yeast employed is one which is specifically adapted for the preparation of active dried yeast rather than compressed yeast. The type of culture generally utilized in the preparation of active dried yeast is classified as Bios No. 23, which classification is made according to the bios response procedure published by Schultz and Atkin in "Archives of Biochemistry" Vol. 14, p. 369, Aug. 1947.

After propagation, the yeast is separated from the other constituents of the growth media by centrifugation or like means and optionally is subjected to one or more washings with water. The product so derived is generally known in the art as yeast cream, and will typically have a solids content of from about 10 to about 20%. The yeast cream so obtained is then treated with the osmotically active solution of the magnesium or calcium salt in the manner described above.

Advantageously, the treatment is carried out by bringing the yeast cream and osmotically active solution together in any appropriate manner and subjecting the resulting mixture to agitation over a predetermined period of time. The actual time of treatment, most appropriate for any particular combination of type of yeast cream and magnesium or calcium salt, can be readily determined by a process of trial and error. Advantageously, the treatment time is within the range of about 2 minutes to about 30 minutes although the actual time employed in any given instance is not known to be critical to the success of the improved process of the invention.

When the treatment of the yeast cream with the salt solution is complete the yeast is isolated from the mixture, preferably by rotary vacuum filtration means. The resulting yeast filter cake is advantageously washed, preferably on the filtration means, to obtain a compressed yeast before being subjected to the final stages of drying. When processed according to the preferred procedures outlined above, active dry yeasts obtained employing a calcium salt as the osmotic agent will have residual calcium content of from about 0.13 to about 0.19 percent, and those obtained employing a magnesium salt will have a residual magnesium content of from about 0.15 to about 0.19 percent, all based on the weight of dry solids.

It is advantageous to add a swelling and/or a wetting agent to the yeast filter cake to improve drying and to ensure non-damaging rehydration, especially when it is desired to add the active dried yeast to flour without hydrating it first. Advantageously, the amount of such compounds incorporated into the yeast before drying is within the range of about 0.5 to about 2.5 percent by weight based on the weight of the yeast solids. The incorporation of these compounds into the compound yeast filter cake is readily accomplished, preferably prior to extrusion, by means known to the art, and is discussed, for example in U.S. Pat. No. 4,370,420, and Japanese Patent Application No. 22471/1976, the disclosures of which are incorporated herein by reference.

Illustrative of suitable swelling agents are methylcellulose, carboxymethylcellulose, hydroxypropyl cellulose, and wetting agents such as esters of saturated or unsaturated fatty acids. Illustrative of suitable wetting agents are sorbitan fatty esters such as sorbitan monolaurate, monostearate, monopalmitate and monooleate and the like, glycerol fatty acid esters such as the monostearate, monopalmitate, distearate and the like, as well as esters with lower organic acids such as acetic acid, lactic acid, citric acid, tartaric acid, diacetyltartaric acid and the like; and propylene glycol fatty acid esters such a propylene glycol monostearate. Mixtures of two or more of such compounds can be employed if desired.

The final drying of the yeast filter cake is accomplished by methods generally employed in the art, as set forth in the above documents which are incorporated herein by reference. Such methods generally involve extruding the compressed yeast through an appropriate die to produce strands of material which are then subjected to drying under controlled conditions. For example, the strands can be extruded and then dried in a fluidized bed drier, in one or a plurality of stages, or on a moving conveyor belt which carries the strands through a number of dryer zones maintained at temperatures effective for the purpose. The temperature and residence time of the yeast in the drier are adjusted as known in the art so that the moisture level of the yeast is efficiently reduced to the desired level without causing excessive reduction in yeast activity. The active dried yeast so obtained is then packaged in an appropriate manner.

The active dried yeast prepared in accordance with the invention is characterized by improved retention of leavening activity (both in sugar-containing doughs and no-sugar doughs) during the drying process as compared with active dried yeast prepared in the same manner but without observing the requirements set forth above in terms of the specific osmotically active salt solutions.

The following examples describe the manner and process of making and using the invention and set forth the best mode contemplated by the inventors of carrying out the invention, but are not to be construed as limiting.

EXAMPLE I

According to this example, five 800 cc aliquots of a yeast cream are taken and treated to show the improvement in activity according to the invention.

In this example and all following examples the yeast cream employed as starting material is prepared by cultivating a strain (Bios Number 23) of *Saccharomyces cerevisiae* in a wort of molasses and other nutrients (including ammonia, phosphoric acid, and trace elements such as B-vitamins and minerals) using procedures conventional in the art.

Aliquot 1 is admixed with 150 ml of water containing 2 percent by weight, based on weight of yeast cream, of sodium chloride (about 0.79 percent $Na^+$ by weight of the yeast cream) and held for 20 minutes with constant agitation. The resulting product is divided into four equal parts by volume and each part is filtered on a separate Buchner funnel. Once the liquid disappears from the surface of each of the solids on the funnel the solids are washed on the funnel with 100 ml of water. The solids are freed of external water to the extent possible on each of the four funnels and then removed, combined as quickly as possible and subjected to pressing in a Carver Press at 12,000 psi for 8 minutes to simulate a commercial filtration process.

Aliquots 2, 3 and 4 of the yeast cream are admixed with 150 ml of water containing respectively: 1.5 percent by weight, based on yeast cream, of potassium chloride (about 0.79 percent $K^+$ based on yeast cream); 2.2 percent by weight, based on yeast cream, of calcium chloride (about 0.79 percent $Ca^{++}$ based on yeast cream); and 3.1 percent by weight, based on yeast cream, of magnesium chloride (about 0.79 percent $Mg^{++}$ based on yeast cream). The mixtures so obtained are then treated exactly as described above for aliquot 1 to obtain compressed yeast therefrom.

A fifth aliquot (800 cc) of yeast cream is taken as a control and is subjected to the above described process for isolation of compressed yeast therefrom without preliminary treatment with any form of salt solution.

A portion (350 g) of each of the compressed yeasts so obtained is then treated with an aqueous emulsion containing wetting and swelling agents as described above before being extruded twice as strands through an 0.023" die. A portion (200 g) of strands from each yeast specimen is finally dried in a fluid bed dryer. Specimens of each aliquot taken both before and after the drying step are tested for activity (in terms of volume of gas evolved) for straight and high sugar doughs in dough analogue compositions containing flour, sugar, salt, non-fat dry milk and selected yeast foods by measuring the amount (cc) of carbon dioxide evolved over a standard time period at a controlled temperature.

The results of the above tests on the various extracted aliquots and the control sample of yeast are shown in TABLE 1 below. It will be sen that the aliquots which have been treated with calcium chloride and magnesium chloride show a substantially lower loss in activity in the drying step as compared to the aliquots which have been treated with sodium chloride and potassium chloride (at the same level of concentration of cation as the calcium and magnesium chloride treated aliquots).

In this example and all other examples, the activities of the yeasts are expressed as comparative numbers based on a scale of 1 to 100, with 100 being the activity in the straight dough test of the control (no salt) sample in the compressed (not dried) form.

TABLE I

| | Aliquots | | | | |
|---|---|---|---|---|---|
| Test: stage | 1 (NaCl) | 2 (KCl) | 3 (CaCl$_2$) | 4 (MgCl$_2$) | Control (No Salt) |
| Compressed yeast: | | | | | |
| Straight dough | 101 | 108 | 98 | 109 | 100 |
| High sugar | 80 | 83 | 78 | 81 | 79 |
| Dried yeast stage: | | | | | |
| Straight dough | 82 | 79 | 99 | 102 | 85 |
| High sugar | 58 | 55 | 75 | 77 | 62 |
| % retention of activity | | | | | |
| Straight: | 81 | 74 | 100 | 94 | 85 |
| High sugar: | 72 | 66 | 97 | 95 | 78 |

EXAMPLE 2

The experiments described in Example 1 are repeated exactly as described and using the same salt solutions in the same concentrations, but using yeast cream from another batch.

The same tests are carried out on each of the yeasts so produced, both in the compressed stage before the drying step and on the active dried yeast isolated at the end of the drying stage. The results of the tests are set forth in TABLE II below from which it will be seen that the active dried yeast derived using calcium chloride and magnesium chloride shows no significant loss of activity after the drying step. The active dried yeast derived using potassium chloride also shows no significant loss in activity after the drying step, but the levels of activity in both compressed and dried stages are significantly less than those of the former two dried yeasts. The active dried yeast prepared using sodium chloride shows significant loss of activity after the drying process.

TABLE II

| | Aliquots | | | | |
|---|---|---|---|---|---|
| Test: stage | 5 (NaCl) | 6 (KCl) | 7 (CaCl$_2$) | 8 (MgCl$_2$) | Control (No Salt) |
| Compressed yeast: | | | | | |
| Straight dough | 86 | 76 | 81 | 93 | 100 |
| High sugar | 67 | 56 | 63 | 70 | 77 |
| Dried yeast stage: | | | | | |
| Straight dough | 76 | 79 | 84 | 90 | 79 |
| High sugar | 58 | 57 | 62 | 68 | 58 |
| % retention of activity | | | | | |
| Straight | 88 | 100 | 100 | 97 | 79 |
| High sugar | 87 | 100 | 100 | 98 | 75 |

EXAMPLE 3

The experiments described in Example 1 are again repeated exactly as described, using the same reactants in the same proportions but using a different batch of yeast cream. The same tests are carried out on each of the yeasts so produced, both on the compressed stage before drying and on the active dried yeast isolated at the end of the drying stage. The results of the tests are set forth in TABLE III below from which it will again be seen that the active dried yeasts prepared using calcium chloride and magnesium chloride retain substantially all activity after drying whereas those prepared using sodium chloride and potassium chloride show significant loss of activity after drying.

TABLE III

| | Aliquots | | | | |
|---|---|---|---|---|---|
| Test: stage | 9 (NaCl) | 10 (KCl) | 11 (CaCl$_2$) | 12 (MgCl$_2$) | Control (No Salt) |
| Compressed yeast: | | | | | |
| Straight dough | 104 | 89 | 100 | 98 | 100 |
| High sugar | 75 | 71 | 74 | 73 | 73 |
| Dried yeast stage: | | | | | |
| Straight dough | 50 | 75 | 88 | 84 | 76 |
| High sugar | 33 | 47 | 62 | 61 | 55 |
| % retention of activity | | | | | |
| Straight | 51 | 84 | 88 | 86 | 76 |
| High sugar: | 57 | 67 | 84 | 84 | 75 |

EXAMPLE 4

The experiments described in Example 1, except that in which potassium chloride was used in the salt treatment, are again repeated exactly as described at the same concentrations of the various salts, on a different batch of yeast cream. The same tests are carried out on the compressed yeasts and the active dried yeasts and the results are summarized in TABLE IV below. The experiments again confirm the superior retention of activity after the drying step in the case of the yeasts derived using magnesium chloride and calcium chloride as compared with samples wherein sodium chloride is used in the initial treatment of the yeast cream.

TABLE IV

| | Aliquot | | | |
|---|---|---|---|---|
| Test: stage | 13 (NaCl) | 14 (CaCl$_2$) | 15 (MgCl$_2$) | Control (No Salt) |
| Compressed yeast: | | | | |

TABLE IV-continued

| Test: stage | Aliquot | | | |
|---|---|---|---|---|
| | 13 (NaCl) | 14 (CaCl₂) | 15 (MgCl₂) | Control (No Salt) |
| Straight dough | 107 | 102 | 106 | 100 |
| High sugar | 84 | 79 | 83 | 79 |
| Dried yeast stage: | | | | |
| Straight dough | 95 | 106 | 105 | 109 |
| High sugar | 72 | 81 | 82 | 81 |
| % retention of activity | | | | |
| Straight | 89 | 100 | 100 | 100 |
| High sugar: | 86 | 100 | 99 | 100 |

EXAMPLE 5

The experiments described in Example 1 are repeated exactly as described but using aliquots of a yeast cream derived from a different batch of yeast produced using the same yeast strain as that of Example 1. The same tests are carried out on the compressed yeasts and the active dried yeasts and the results are summarized in TABLE V below. The experiments again confirm the superior retention of activity after the drying step in the case of the yeasts prepared using magnesium chloride and calcium chloride as compared with samples prepared using sodium chloride in the initial treatment of the yeast cream.

TABLE V

| Test: stage | Aliquot | | | |
|---|---|---|---|---|
| | 16 (NaCl) | 17 (CaCl₂) | 18 (MgCl₂) | Control (No Salt) |
| Compressed yeast: | | | | |
| Straight dough | 110 | 105 | 101 | 100 |
| High sugar | 84 | 85 | 82 | 82 |
| Dried yeast stage: | | | | |
| Straight dough | 88 | 106 | 114 | 99 |
| High sugar | 65 | 86 | 81 | 77 |
| % retention of activity | | | | |
| Straight | 80 | 100 | 100 | 99 |
| High sugar: | 80 | 100 | 99 | 94 |

We claim:

1. In a process for the preparation of active dried yeast comprising the steps of treating a yeast cream with an osmotically active salt solution, filtering to separate yeast from the yeast cream, washing the separated yeast with water, and drying the washed yeast, the improvement which comprises employing as said osmotically active salt solution an aqueous solution comprising calcium or magnesium chloride present in a concentration such that the amount of calcium or magnesium cation present is from about 0.1 percent to about 5 percent by weight based on the weight of yeast cream being treated.

2. A process according to claim 1 wherein said amount of metal cation is from about 0.2 percent to about 2 percent by weight based on the weight of yeast cream being treated.

3. A process for the preparation of an active dried yeast which comprises the steps of:
   subjecting a yeast cream to the action of an osmotically active aqueous solution of a soluble salt selected from the group consisting of magnesium and calcium chlorides the magnesium or calcium cation being present in an amount from about 0.1 percent to about 5 percent by weight based on the weight of yeast cream being treated;
   filtering to separate yeast from the yeast cream; washing the separated yeast with water;
   extruding the washed yeast in the form of strands; and drying said strands.

4. A process according to claim 3 wherein said osmotically active aqueous solution contains magnesium chloride in an amount such that the content of magnesium cation is within the range of about 0.2 percent by weight to about 2 percent by weight based on weight of yeast cream being treated.

5. A process according to claim 3 wherein said osmotically active aqueous solution contains calcium chloride in an amount such that the content of calcium cation is within the range of about 0.2 percent by weight to about 2 percent by weight based on weight of yeast cream being treated.

6. A product produced according to the process of claim 1.

7. A product produced according to the process of claim 4.

8. A product produced according to the process of claim 5.

9. An active dry yeast prepared in accordance with claim 1 and having a magnesium content of from about 0.15 to about 0.19 based on the dry weight of the yeast.

10. An active dry yeast prepared in accordance with claim 1 and having a calcium content of from about 0.13 to about 0.19 based on the dry weight of the yeast.

* * * * *